US00PP12586P2

(12) United States Plant Patent
Gross

(10) Patent No.: US PP12,586 P2
(45) Date of Patent: Apr. 30, 2002

(54) POINSETTIA PLANT NAMED 'FIREWORK'

(75) Inventor: Eduard Gross, Blanzac (FR)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/563,936

(22) Filed: May 4, 2000

(51) Int. Cl.[7] ..... A01H 5/00
(52) U.S. Cl. ..... Plt./307

(58) Field of Search ..... Plt./307

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Poinsettia plant named 'Firework', characterized by its red and sharply pointed flower bracts that are held somewhat upright; dark green leaves; compact, uniform, upright and outwardly spreading plant habit; very freely branching habit; early flowering; and excellent post-production longevity.

2 Drawing Sheets

BACKGROUND OF THE INVENTION

The present Invention relates to a new and distinct cultivar of Poinsettia plant, botanically known as *Euphorbia pulcherrima* Willd., and hereinafter referred to by the name 'Firework'.

The new Poinsettia is a naturally-occurring whole plant mutation of the *Euphorbia pulcherrima* Willd. cultivar Red Baron, disclosed in U.S. Plant Pat. No. 10,162. The new Poinsettia was discovered and selected by the Inventor in March, 1997, in a controlled environment in Blanzac, France. Compared to plants of the parent cultivar, plants of the new Poinsettia have lighter red flower bract color.

Asexual reproduction of the new Poinsettia by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Firework'. These characteristics in combination distinguish 'Firework' as a new and distinct cultivar:

1. Bright red and sharply pointed flower bracts that are held somewhat upright.
2. Dark green leaves.
3. Compact, uniform, upright and outwardly spreading plant habit.
4. Very freely branching habit.
5. Early flowering.
6. Excellent post-production longevity.

Plants of the new Poinsettia can be compared to plants of the Poinsettia cultivar Peterstar, disclosed in U.S. Plant Pat. No. 8,259. In side-by-side comparisons conducted in Encinitas, Calif., plants of the new Poinsettia differed from plants of the cultivar Peterstar in the following characteristics:

1. Plants of the new Poinsettia are taller and more uniform in plant habit than plants of the cultivar Peterstar.
2. Plants of the new Poinsettia are more freely branching than plants of the cultivar Peterstar.

3. Plants of the new Pointsettia have darker green leaves than plants of the cultivar Peterstar.
4. Plants of the new Poinsettia root more quickly than plants of the cultivar Peterstar.
5. Flower bracts of the new Poinsettia are shorter, narrower more pointed and held more upright than flower bracts of the cultivar Peterstar.
6. Flower bract color of the new Poinsettia is more crimson red than flower bract color of the cultivar Peterstar.
7. Plants of the new Poinsettia have longer post-production longevity than plants of the cultivar Peterstar.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the actual colors of the new Poinsettia.

The photograph at the top of the first sheet comprises a side perspective view of a typical plant of 'Firework'.

The photograph at the bottom of the first sheet comprises a top perspective view of a typical plant of 'Firework'.

The photograph on the second sheet is a close-up view of typical bracts and leaves of 'Firework' (left) and 'Peterstar' (right).

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a glass-covered greenhouse with day temperatures about 21 to 27° C., night temperatures about 18 to 20° C., and light levels about 4,000 foot-candles. Plants were grown in 16.5-cm pots, pinched one time, and flowered under naturally lengthening nights during the fall.

In the following description, color references are made to The Royal Horticultural Society Colour Chart except where general terms of ordinary dictionary significance are used.

Botanical classification: *Euphorbia pulcherrima* Willd. cultivar Firework.

Parentage: Naturally-occurring whole plant mutation of *Euphorbia pulcherrima* Willd. cultivar Red Baron, disclosed in U.S. Plant Pat. No. 10,162.

Propagation:

*Type cutting.*—Terminal cuttings.

*Time to initiate roots.*—Summer: About 7 days at 24° C. Winter: About 10 days at 22° C.

*Time to develop roots.*—Summer: About 26 days at 24° C. Winter: About 26 days at 22° C.

*Rooting habit.*—Thick, freely branching.

Plant description:

*Plant form.*—Inverted triangle, top of plant rounded; mounding.

*Growth habit.*—Compact, upright and outwardly spreading. Very freely branching. Branching is enhanced by removing the shoot apex. Vigorous.

*Plant height.*—About 29 cm.

*Crop time.*—From unrooted cuttings to a flowering plant in a 16.5-cm container, about 17 weeks are required.

*Stem description.*—Number of lateral branches: About 9 lateral branches develop after removal of the terminal apex. Lateral branch length: About 19 cm. Internode length: About 1.25 cm. Stem color: 146A; distally, tinged with 59B.

*Foliage description.*—Quantity of leaves per lateral branch: About 9. Length: About 12 cm. Width: About 6.5 cm. Shape: Mostly ovate. Apex: Acuminate. Base: Acute. Margin: Entire. Texture: Smooth; glabrous. Color: Young foliage, upper surface: 146A. Young foliage, lower surface: 146B. Mature foliage, upper surface: Darker than 147A. Mature foliage, lower surface: 147B. Venation, upper surface: 144B. Venation, lower surface: 146B. Petiole: Length: About 4 cm. Diameter: About 3 mm. Color: 59A.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long night conditions. Early flowering, response time is about 8.5 weeks.

*Quantity of inflorescences.*—One per lateral branch, usually about 9 per plant.

*Inflorescence size: Diameter: About* 32 cm. Height (depth): About 5 cm.

*Flower bracts.*—Quantity of flower bracts per inflorescence: Usually about 16 primary bracts and about 7 smaller secondary bracts per inflorescence. Length, largest bracts: About 17 cm. Width, largest bracts: About 8 cm. Shape: Mostly ovate. Apex: Acuminate. Base: Acute. Margin: Entire. Texture: Smooth. Aspect: Mostly flat. Color: Developing, upper surface: 46A. Developing, lower surface: 46B. Mature, upper surface: 45A; color does not fade with subsequent development. Mature, lower surface: 45B to 45C.

*Cyathia.*—Quantity: Usually about 14 per corymb. Diameter of cyathia cluster: About 2 by 3 cm. Length: About 1 cm. Width: About 6 mm. Color: Immature: 144B. Mature: 144A.

*Peduncle.*—Length: About 4 mm. Aspect: Strong, erect. Color: 144A.

*Reproductive organs.*—Stamens: Stamen number: Typically about 7 fertile stamens and numerous stamenodes per cyathium. Anther shape: Oblong. Anther length: About 1 mm. Anther color: 46A. Amount of pollen: Scarce. Pollen color: 8B. Pistils: Length: About 9 mm. Stigma color: 46A. Style color: 46A. Nectary color: 33A.

Disease resistance: Resistance to pathogens common to Poinsettias has not been observed on plants grown under commercial conditions.

Post-production longevity: Generally plants maintain good substance and bract color for about six weeks under interior conditions.

It is claimed:

1. A new and distinct cultivar of Pointsettia plant named 'Firework', as illustrated and described.

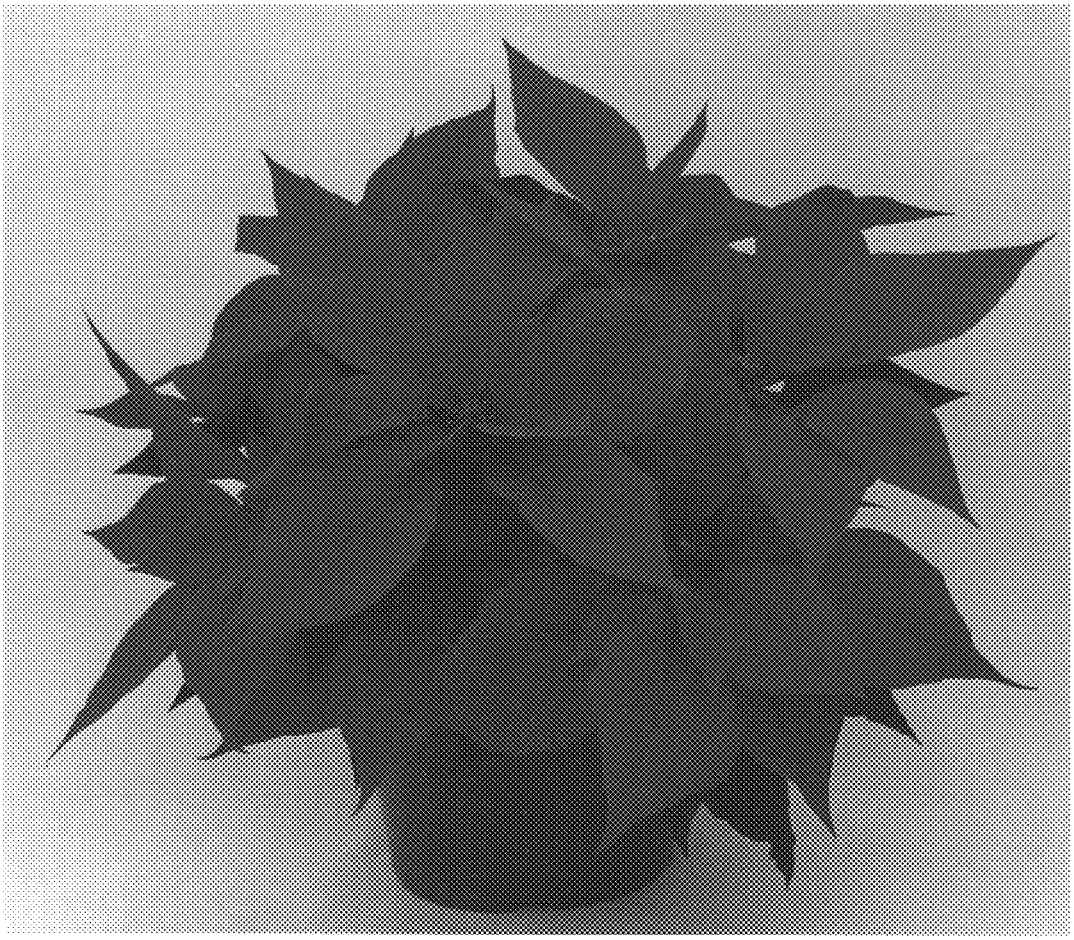
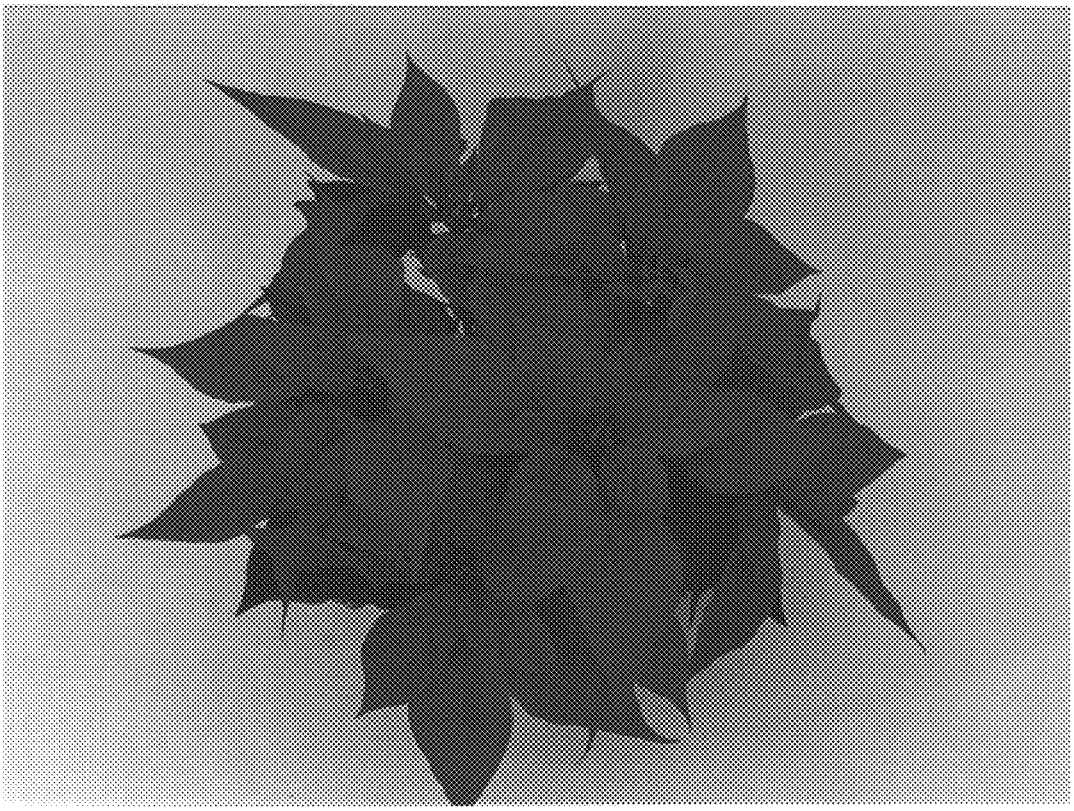

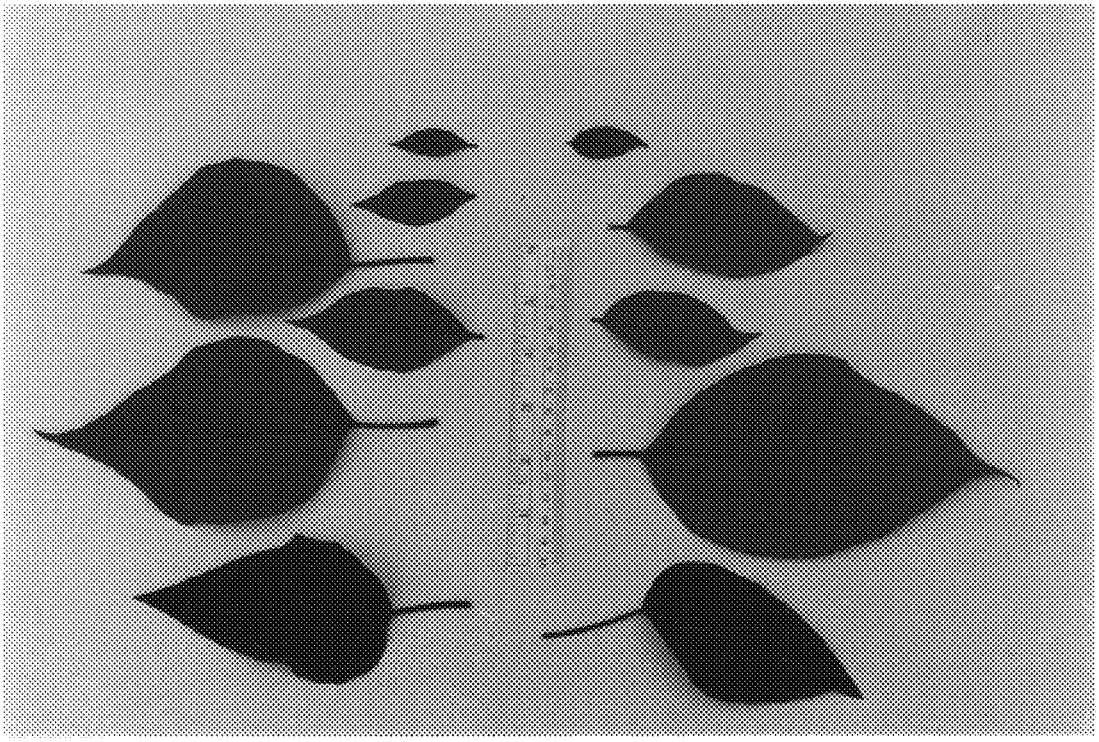

* * * * *